United States Patent [19]

Wandrey et al.

[11] 4,326,031
[45] Apr. 20, 1982

[54] PROCESS FOR THE CONTINUOUS ENZYMATIC CHANGE OF WATER SOLUBLE α-KETOCARBOXYLIC ACIDS INTO THE CORRESPONDING α-HYDROXYCARBOXYLIC ACIDS

[75] Inventors: Christian Wandrey; Rolf Wichmann, both of Jülich; Wolfgang Leuchtenberger, Bruchköbel; Maria-Regina Kula, Wolfenbüttel; Andreas Bückmann, Braunschweig-Stöckheim, all of Fed. Rep. of Germany

[73] Assignee: Degussa AG, Frankfurt, Fed. Rep. of Germany

[21] Appl. No.: 172,444

[22] Filed: Jul. 25, 1980

[30] Foreign Application Priority Data

Jul. 25, 1979 [DE] Fed. Rep. of Germany ....... 2930087

[51] Int. Cl.³ .................................................. C12P 7/42
[52] U.S. Cl. .................................... 435/146; 435/180; 435/288
[58] Field of Search ................. 435/146, 180, 26, 288

[56] References Cited

U.S. PATENT DOCUMENTS 4,229,529 10/1980 Michal et al. ........................ 435/26
4,266,026 5/1981 Breslav ............................... 435/288

FOREIGN PATENT DOCUMENTS 648917 9/1962 Canada ............................... 435/146

OTHER PUBLICATIONS

Immobilized Enzymes, 1978, Wiley & Sons, N. Y., Chibata, Editor, pp. 80, 81.

*Primary Examiner*—Hiram Bernstein
*Attorney, Agent, or Firm*—Cushman, Darby & Cushman

[57] ABSTRACT

Water soluble α-ketocarboxylic acids are continuously converted in a membrane reactor into the corresponding α-hydrocarboxylic acids. The conversion takes place in the presence of a substrate specific dehydrogenase and of a nicotinamide-adenine-dinucleotide (NAD+/NADH) enlarged in molecular weight through linkage to a water soluble polymer as coenzyme. Simultaneously NADH is regenerated continuously from NAD+ in presence of a formate dehydrogenase and from formate ion. The membrane must have a mean pore diameter of 1 to 3 nm. As coenzyme there is employed 0.1 to 10 mmol/l of NAD+/NADH present bound to a water soluble polymer having an average molecular weight between 500 and 50,000. There is continuously supplied to the reactor a substrate stream which contains 50 to 100% of the maximum amount soluble, but not over 2,000 mmol/l, of the reacting α-ketocarboxylic acid in the form of a water soluble salt and 100 to 6,000 mmol/l of a formate. There is maintained over the membrane a differential pressure of 0.1 to 15 bar. There is continuously drawn off behind the membrane a filtrate stream containing the α-hydroxy acid formed.

14 Claims, No Drawings

4,326,031

PROCESS FOR THE CONTINUOUS ENZYMATIC CHANGE OF WATER SOLUBLE α-KETOCARBOXYLIC ACIDS INTO THE CORRESPONDING α-HYDROXYCARBOXYLIC ACIDS

BACKGROUND OF THE INVENTION

The invention is directed to a process for the continuous enzymatic conversion of water soluble α-ketocarboxylic acid into the corresponding α-hydrocarboxylic acid in the presence of a substrate specific dehydrogenase, ammonium ions and nicotinamide-adenine-dinucleotide (NAD+/NADH) of increased molecular weight by bonding to a water soluble polymer in a membrane reactor equipped with an ultrafil-tration membrane with simultaneously regeneration of NADH from NADH+ by means of formate ion in the presence of a formate dehydrogenase.

Enzymatic conversions in membrane reactors indeed have been investigated for a long time but customarily without forced convection of the reaction mixture over the membrane without continuous regeneration of a coenzyme and with very small substrate concentrations. The use of such conversions on a production scale suffered because previously continuous carrying out of the process was not possible and there could only be obtained small space-time-yields.

SUMMARY OF THE INVENTION

The process of the invention comprises employing a membrane reactor, the membrane of which has a mean pore diameter of 1 to 3 nm and which contains a solution of the formate dehydrogenase, the substrate specific dehydrogenase and from 0.1 to 10 mmol/l of NAD+/NADH present bound to a water soluble polymer having an average molecular weight between 500 and 50,000, continuously supplying an aqueous solution having 50 to 100% of the maximum amount soluble, but not over 2,000 mmol/l, of the α-ketocarboxylic acid to be converted in the form of a water soluble salt as substrate and from 100 to 6,000 mmol/l of a formate, maintaining a differential pressure over the membrane of 0.1 to 15 bar and continuously drawing off behind the membrane a filtrate stream containing the α-hydrocarboxylic acid formed.

The process of the invention permits water soluble α-ketocarboxylic acids to be converted continuously and with high space-time-yields into the corresponding α-hydroxycarboxylic acids and is therefore useful for a cost favorable production of these aminoacids.

As reaction vessel there is used an ultrafiltration membrane which membrane serves to retain in the reactor the enzyme employed and the necessary coenzyme for the conversion, but permits the lower molecular weight product and the unconverted substrate to pass through. The membrane reactor can also be formed as a so-called flat membrane reactor. In this type of reactor, for example, it can be a flat cylindrical vessel on which there is placed a cover made tight by means of an O-ring. The relatively stretched flat membrane is attached together with the O-ring. The substrate stream is supplied by a metering pump to the reaction space lying below the membrane, which reactor space is suitably equipped with a stirring device, e.g., a magnetic stirrer. The filtrate stream containing the product leaves the reaction space through the membrane and a plate provided with bores for the purpose of avoiding its mechanical stresses and is drawn off out of the cover. A so-called hollow fiber-membrane reactor, in which a hollow fiber bundle made of ultrafiltration membranes, a so-called hollow fiber module, at the place the flat membrane enters is then advantgeous if because of the geometric arranged there are to be attained higher Reynolds numbers of the fluid parallel to the membrane and therewith lower coating of the membrane with enzyme proteins. In this type of reactor, for example, it is a matter of a type of loop reactor, which consists of a reaction container, a circulation pump and the hollow fiber module. The substrate stream is supplied to the reaction container by means of a metering pump. In this the reaction mixture is pumped around whereby the pumped around stream is in the proportion to the substrate stream at least about 100:1, in order to keep the coating of the hollow fiber membranes with enzyme protein as small as possible. The filtrate stream containing the product passes through the hollow fiber membranes and is collected behind these and drawn off. There are used for the process of the invention membranes which have a mean pore diameter of 1 to 3 nm. Suitable materials for the membranes, for example, are acetyl celluloses, polyamides, e.g., nylon-6,6 polysulfones or modified polyvinyl alcohols.

The membrane reactor contains a solution of a formate dehydrogenase, a substrate specific dehydrogenase and NAD+/NADH greatly enlarged in molecular weight. The formate dehydrogenase is suitably employed in such an amount that its activity is at least 12,000 μmol/l minute. Upwardly the amount of its addition suitably should be so limited that the protein concentration is maximally about 20 g/l. The substrate specific dehydrogenase is suitably added in such an amount that the ratio of the activities of formate dehydrogenase and substrate specific dehydrogenase is between 1:1 and 1:5.

The required NAD+/NADH as coenzyme in the process of the invention must be enlarged to such an extent in molecular weight that it is indeed still water soluble in order to permit a homogeneous catalysis, on the other hand, however, together with the two enzymes to be safely held back by the membrane. For this purpose the water soluble polymer have an average molecular weight between 500 and 50,000, preferably between 1,500 and 10,000. Examples of usable polymers are dextrans, polyether polyols such as polyethylene glycol and polypropylene glycol, polyethylenimine, polyacrylamide or mixed polymers such as methyl vinyl ether-maleic anhydride mixed polymers. Polyethylene glycols are preferred. The production of the coenzyme of enlarged molecular weight, for example, can take place in such manner that the coenzyme in its oxidized form first is reacted at the N(1)-atom with an alkylating agent, which introduces a further functional group, which makes possible the coupling to the polymer. As such alkylating agents there can be used, for example, halocarboxylic acids such as iodoacetic acid, bromoacetic acid, chloroacetic acid, epoxycarboxylic acids such as 3,4-epoxybutyric acid, lactones such as β-propiolactone or aziridines such as ethyleimine. The N(1)-derivative obtained is subsequently coupled to the water soluble polymer, in which if necessary there are introduced previously groups, e.g., carboxyl groups, capable of reacting with the N(1)-derivative. The coupling is carried out with the help of the Carbodiimide method (see Cuatrecanas, J. Biol. Chem., Volume 245, page 3059 (1970)). The coupled product obtained is then reduced to the corresponding NADH derivative, through a Dimroth-arrangement converted into the N(6)-derivative and in a given case again oxidized to the corresponding NAD+-derivative. The coenzyme having an enlarged molecular weight is added in such an amount that the concentration of NAD+/NADH is 0.1 to 10 mmol/l, preferably 1 to 7 mmol/l.

The membrane reactor is continuously supplied with an aqueous solution of the substrate and formate ions. The concentration of the substrate should amount to 50 to 100% of the maximal possible concentration, however, it is not permitted to exceed 2,000 mmol/l, preferably not over 1,000 mmol/l. The concentration of formate ions is between 100 and 6,000 mmol/l, preferably between 300 and 2,000 mmol/l. As formates there are preferably used sodium or potassium formate.

The α-ketocarboxylic acid employed is reduced to the corresponding α-hydrocarboxylic acid in the presence of the substrate specific dehydrogenase and the reduced form of the coenzyme (NADH) in the reaction space of the membrane reactor, wherein the coenzyme is converted into the oxidized form (NADH+). However, simultaneously the reduced form of the coenzyme (NADH) is continuously regenerated through the formate ion present in the presence of the formate dehydrogenase, whereby the formate ion is oxidized to carbon dioxide.

During the conversion there must be maintained over the membrane a pressure differential of 0.1 to 15 bar, preferably 0.2 to 3 bar, which is attained by use of a correspondingly dimensioned metering pump for the substrate solution being supplied and in a given case through a butterfly valve in the filtrate stream behind the membrane. The pressure differential causes a filtrate stream to pass through the membrane with the desired velocity. The absolute pressure on the delivery side of the membrane should suitably be so adjusted that even with powerful stirring or repumping into the reaction space before the membrane for production of a strong turbulence along the membrane and therewith for the avoidance of a coating of the membrane with the enzyme or the coenzyme of increased molecular weight the pressure at no place is reduced to such an extent that there is a degassing of the reaction mixture on the delivery side. The membrane reactor is maintained at a customary temperature between 25° and 50° C. for enzymatic conversions. Likewise the pH of the reaction mixture during the conversion is maintained in the customary range of 5 to 9 for enzymatic conversions.

Suitable formate dehydrogenases for carrying out the process of the invention can be isolated, for example, from *Candida boidinii* or from *Pseudomonas oxalaticus*. Examples of substrate specific dehydrogenase usable in the process of the invention are L-lactate dehydrogenase and D-lactate dehydrogenase. With their help, for example, pyruvic acid can be converted into lactic acid, phenyl pyruvic acid into L- or D-phenyl lactic acid, 2-oxo-4-methylvaleric acid into L- or D-2-hydroxy-4-methylvaleric acid, 2-oxo-3-methylvaleric acid into L- or D-2-hydroxy-3-methyl valeric acid, or 2-oxo-3-methylbutyric acid into L- or D-2-hydroxy-3-methyl butyric acid or 2-oxo-valeric acid into L- or D-2-hydroxyvaleric acid. Suitably the reacting α-ketocarboxylic acids are employed in the form of their sodium or potassium salts, e.g., sodium pyruvate or potassium 2-oxo-valerate. Since in the conversion of α-ketocarboxylic acids, e.g., α-ketoalkanoic acids or phenylpyruvic acid into the corresponding α-hydroxycarboxylic acids, e.g., hydroxyalkanoic acids or phenyl acetic acid an optionally active center is newly formed, the product concentration in the filtrate stream can be measured continuously with the help of a polarimeter. The α-hydroxycarboxylic acid formed can be obtained from the filtrate in known manner.

This can be produced, for example, by separating the α-hydroxycarboxylic acid from the unreacted α-ketocarboxylic acid by means of a basic ion exchanger which makes the most of different acid strengths. The different solubility of salts, particularly the calcium salt, in many cases makes possible a separation through fractional crystallization. In a given case the different polarity can also be drawn on for separation by extraction with a suitable solvent.

The process can comprise, consist essentially of or consist of the steps set forth and the material employed can comprise, consist essentially of or consist of those stated.

Unless otherwise indicated all parts and percentages are by weight.

In the following examples the process of the invention will be explained in more detail in connection with the conversion of phenyl pyruvic acid into D-phenyl lactic acid.

DETAILED DESCRIPTION OF THE INVENTION

Example 1

A flat membrane reactor maintained at a temperature of 25° C. and having a volume of 10 ml which was equipped with a magnetic stirrer and an ultrafiltration membrane having a diameter of 62 mm with a nominal exclusion limit of 5,000 (supplier: Amicon, Written; Type DM 5), for sterilization was rinsed well with an aqueous formaldehyde solution for about 20 hours with the help of a metering pump adjusted to a conveying velocity of 4 ml/hours. Subsequently during about a further 20 hours the formaldehyde solution was displaced by distilled water. Then there was supplied, likewise with a conveying speed of 4 ml/hour for about 10 hours a substrate solution filtered over a sterile filter (0.2μ). The substrate solution contained 100 mmol/l of sodium phenyl pyruvate, and 200 mmol/l of sodium formate, as well as 100 mmol/ of sodium phosphate as a buffer, which solution was adjusted to pH 8 with sodium hydroxide solution. Then in place of the substrate solution there were metered in 2.5 ml of a coenzyme solution, which contained 4 mmol/l NADH bonded to a polyoxyethylene with a mean molecular weight of 10,000 and 50 mmol/l of a phosphate buffer to maintain a pH of 7. After the complete addition of the coenzyme solution there was again supplied the above substrate solution with a conveying speed of 4 ml/hour. Then there was added to the reaction space before the membrane through a lateral bore by means of an injector 29.63 mg of formate hydrogenase (activity 2.70 μmol/mg×minute with formate as substrate, 25° C. and pH 7) in the form of an aqueous glycerine solution (50 weight percent glycerine; 10 mg formate dehydrogenase/ml) and 0.8 mg D-lactate dehydrogenase (activity 100 μmol/mg×minute with phenyl pyruvate as substrate, 25° C. (and pH 7) in the form of an aqueous ammonium sulfate solution (3.2 mol/l (NH$_4$)$_2$SO$_4$; 5 mg D-lactate dehydrogenase/ml). At the control selected the ratio of the activities of formate dehydrogenase and D-lactate dehydrogenase was 1:1. The conversion was followed continuously with the help of a polarimeter flow cell constructed in the filtrate stream. The pressure differential over the membrane at the beginning amounted to 1.0 bar, increased gradually to 1.7 bar and then remained constant. Within an operating time of, in all, about 160 hours there were obtained 8.36 mmol of D-phenyl lactic acid. The maximum rate of conversion was 0.068 mmol of D-phenyl lactic acid.

The entire disclosure of German priority application No. P 29 30 087.8 is hereby incorporated by reference.

What is claimed is:

1. A process for continuously enzymatically converting water soluble α-ketocarboxylic acids in a membrane reactor equipped with a mean pore diameter of 1–3 nm into the corresponding α-hydroxycarboxylic acid comprising carrying out the conversion in the presence of a substrate specific dehydrogenate, a nicotinamide-adenine-dinucleotide (NAD+/NADH) linked to a water soluble polymer of molecular weight 500 to 50,000 as coenzyme while simultaneously regenerating NADH from NAD+ in the presence of a formate dehydrogenase by means of formate ion, there being employed 0.1 to 10 mmol/l of said coenzyme, continuously supplying to the reactor a substrate stream which contains 50 to 100% of the maximum amount soluble, but not over 2,000 mmol/l, of the reacting α-ketocarboxylic acid in the form of a water soluble salt as substrate, and 100 to 6,000 mmol/l of a formate, maintaining over the membrane a differential pressure of 0.1 to 15 bar and continuously drawing off behind the membrane a filtrate stream containing the α-hydroxycarboxylic acid formed.

2. A process according to claim 1 wherein the formate dehydrogenase and the substrate specific dehydrogenase are added in an amount such that the ratio of their activities is between 1:1 and 1:5.

3. A process according to claim 2 wherein the water soluble polymer is a polyethylene glycol.

4. A process according to claim 1 wherein the water soluble polymer is polyethylene glycol.

5. A process according to claim 1 wherein the substrate stream contains not over 1,000 mmol/l of the ketocarboxylic.

6. A process according to claim 5 wherein the formula is present in an amount of 300 to 2,000 mmol/l.

7. A process according to claim 6 wherein the pressure is 0.2 to 3 bar.

8. A process according to claim 7 wherein the ketocarboxylic acid salt is a salt of pyruvic acid, phenyl pyruvic acid, 2-oxo-4-methylvaleric acid, 2-oxo-3-methylvaleric acid, 2-oxo-3-methylbutyric acid or 2-oxovaleric acid.

9. A process according to claim 1 wherein the ketocarboxylic acid salt is a salt of pyruvic acid, phenyl, 2-oxo-4-methylvaleric acid, 2-oxo-3-methylvaleric acid, 2-oxo-3-methylbutyric acid or 2-oxovaleric acid.

10. A process according to claim 8 wherein the ketocarboxylic acid is phenyl pyruvic acid.

11. A process according to claim 10 wherein the substrate specific dehydrogenase is lactate dehydrogenase.

12. A process according to claim 11 wherein the salt is a sodium or potassium salt.

13. A process according to claim 11 wherein the substrate specific hydrogenase is D-lactate dehydrogenase and the polymer is polyethylene glycol.

14. A process according to claim 1 wherein the polymer is dextran, polyether polyol, polyethylenimine, polyacrylamide or method viny ethermaleic anhydride mixed polymer.

* * * * *